(12) United States Patent
Stone

(10) Patent No.: US 9,116,088 B2
(45) Date of Patent: Aug. 25, 2015

(54) METHODS AND SYSTEMS FOR DNA ISOLATION ON A MICROFLUIDIC DEVICE

(71) Applicant: Canon U.S. Life Sciences, Inc., Rockville, MD (US)

(72) Inventor: Michele R. Stone, Apex, NC (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 45 days.

(21) Appl. No.: 13/669,285

(22) Filed: Nov. 5, 2012

(65) Prior Publication Data

US 2013/0224750 A1 Aug. 29, 2013

Related U.S. Application Data

(62) Division of application No. 12/505,195, filed on Jul. 17, 2009, now Pat. No. 8,304,185.

(51) Int. Cl.
| | |
|---|---|
| *C12Q 1/68* | (2006.01) |
| *C07H 21/00* | (2006.01) |
| *G01N 1/34* | (2006.01) |
| *C12N 15/10* | (2006.01) |

(52) U.S. Cl.
CPC .............. *G01N 1/34* (2013.01); *C12N 15/1003* (2013.01)

(58) Field of Classification Search
CPC .................................. C12Q 1/68; C07H 21/00
USPC .......................................... 435/6.1; 536/25.4
See application file for complete search history.

(56) References Cited

U.S. PATENT DOCUMENTS

| | | | |
|---|---|---|---|
| 4,752,564 A | 6/1988 | Hopkins | |
| 5,118,428 A | 6/1992 | Sand et al. | |
| 5,213,796 A * | 5/1993 | Garcea et al. | 424/204.1 |
| 5,284,940 A * | 2/1994 | Lin et al. | 536/25.4 |
| 5,447,864 A * | 9/1995 | Raybuck et al. | 435/270 |
| 5,482,829 A | 1/1996 | Kass et al. | |
| 5,501,954 A | 3/1996 | Mahr et al. | |
| 5,643,455 A | 7/1997 | Kopp et al. | |
| 5,736,033 A | 4/1998 | Coleman et al. | |
| 5,789,243 A | 8/1998 | Boquet | |
| 6,013,439 A * | 1/2000 | Lishanski et al. | 435/6.11 |
| 6,322,983 B1 | 11/2001 | Burgoyne | |
| 6,352,838 B1 | 3/2002 | Krulevitch et al. | |
| 6,387,290 B1 | 5/2002 | Brody et al. | |
| 6,413,747 B1 * | 7/2002 | Kato et al. | 435/91.2 |
| 6,811,695 B2 | 11/2004 | Karp | |
| 6,827,095 B2 | 12/2004 | O'Connor et al. | |
| 6,852,851 B1 | 2/2005 | Tooke et al. | |
| 6,878,271 B2 | 4/2005 | Gilbert et al. | |
| 6,914,137 B2 | 7/2005 | Baker | |
| 6,919,046 B2 | 7/2005 | O'Connor et al. | |
| 6,992,181 B2 | 1/2006 | Tooke et al. | |
| 7,078,191 B1 | 7/2006 | Wanker et al. | |
| 7,111,501 B2 * | 9/2006 | Rocklin et al. | 73/61.52 |
| 7,160,423 B2 | 1/2007 | Chien et al. | |
| 7,192,557 B2 | 3/2007 | Wu et al. | |
| 7,258,976 B2 | 8/2007 | Mitsuhashi | |
| 7,262,283 B2 | 8/2007 | Hendriks et al. | |
| 7,279,134 B2 | 10/2007 | Chan et al. | |
| 7,294,503 B2 | 11/2007 | Quake et al. | |
| 7,320,862 B2 | 1/2008 | Stähler et al. | |
| 7,374,881 B2 | 5/2008 | Mitsuhashi | |
| 7,544,506 B2 * | 6/2009 | Breidford et al. | 435/288.5 |
| 7,939,249 B2 | 5/2011 | Parthasarathy et al. | |
| 8,304,185 B2 * | 11/2012 | Stone | 435/6.1 |
| 8,313,906 B2 * | 11/2012 | Cao et al. | 435/6.1 |
| 2002/0055184 A1 | 5/2002 | Naylor et al. | |
| 2003/0230486 A1 | 12/2003 | Chien et al. | |
| 2005/0042639 A1 | 2/2005 | Knapp et al. | |
| 2005/0142570 A1 | 6/2005 | Parthasarathy et al. | |
| 2005/0142571 A1 | 6/2005 | Parthasarathy et al. | |
| 2005/0142663 A1 * | 6/2005 | Parthasarathy et al. | 436/174 |
| 2006/0024712 A1 | 2/2006 | Baker et al. | |
| 2006/0134599 A1 | 6/2006 | Toner et al. | |
| 2007/0068812 A1 | 3/2007 | Han et al. | |
| 2007/0072229 A1 * | 3/2007 | Bialozynski et al. | 435/6 |
| 2008/0003588 A1 | 1/2008 | Hasson et al. | |
| 2008/0003593 A1 | 1/2008 | Hasson et al. | |
| 2008/0130971 A1 | 6/2008 | Hasson et al. | |
| 2008/0131955 A1 | 6/2008 | Stone | |
| 2008/0176230 A1 | 7/2008 | Owen et al. | |

(Continued)

FOREIGN PATENT DOCUMENTS

| | | |
|---|---|---|
| JP | 2003-516125 A | 5/2003 |
| JP | 2004-519234 A | 7/2004 |
| JP | 2007516722 A | 6/2007 |
| WO | 88/05331 | 7/1988 |
| WO | 2006/004611 A2 | 1/2006 |
| WO | 2007/035498 A2 | 3/2007 |
| WO | 2010/009415 A1 | 1/2010 |

OTHER PUBLICATIONS

Abmayr et al. Unit 12.3 in Current Protocols in Pharmacology 12.3. 1-12.3.13 (2001).*

(Continued)

*Primary Examiner* — Ethan C Whisenant

(74) *Attorney, Agent, or Firm* — Rothwell, Figg, Ernst & Manbeck, P.C.

(57) ABSTRACT

The present invention relates to methods and systems for the isolation of DNA on a microfluidic device and the subsequent analysis of the DNA on the microfluidic device. More specifically, embodiments of the present invention relate to methods and systems for the isolation of DNA from patient samples on a microfluidic device and use of the DNA for performing amplification reactions, such as PCR, and detection, such as thermal melt analysis, on the microfluidic device.

20 Claims, 3 Drawing Sheets

(56) References Cited

U.S. PATENT DOCUMENTS

| | | |
|---|---|---|
| 2009/0053726 A1 | 2/2009 | Owen et al. |
| 2009/0111149 A1 | 4/2009 | Cao |
| 2009/0176899 A1 | 7/2009 | Yoo et al. |
| 2010/0021910 A1 | 1/2010 | Cao et al. |
| 2011/0014605 A1 | 1/2011 | Stone |
| 2011/0136220 A1* | 6/2011 | Nagata ................. 435/317.1 |

OTHER PUBLICATIONS

Graham J.M.,Rapid purification of nuclei from animal and plant tissues and cultured cells. ScientificWorldJournal. 2 : 1551-4 (Jun. 2002).*
Kim et al., Quantitative and qualitative analysis of a microfluidic DNA extraction system using a nanoporous AlO(x) membrane. Lab Chip. 8 (9) : 1516-23 (2008). Epub Jul. 17, 2008.*
Wray et al. Parallel isolation procedures for metaphase chromosomes, mitotic apparatus, and nuclei. Methods in Enzymology 40 : 75 (1975).*
Zhang et al.. PCR microfluidic devices for DNA amplification. Biotechnology Advances 24 : 243 (2006).*
Boom et al., J. Clin. Microbiol., 28(3):495-503 (1990) (abstract).
Bøyum, Nature, 204:793-794 (1964) (abstract).
Breadmore et al., Anal. Chem. 75(8):1880-1886 (2003) (abstract).
Chen et al., Anal. Biochem., 101(2):339-341(1980) (abstract).
Chen et al., Sensors and Actuators B: Chemical, 130(1):216-221 (2008) (abstract).
Cheng et al., Nucleic Acids Research, 24(2):380-385 (1996).
Dignam et al., Nucleic Acids Res., 11(5):1475-1489 (1983).
Li et al., Eukaryotic Cell, 2(5):1091-1098 (2003) (abstract).
Marko et al., Anal. Biochem., 121(2):382-387 (1982) (abstract).
Melzak et al., J. Colloid and Interface Science, 181(2):635-644 (1996) (abstract).
Service, Science, 282(5388):399-401 (1998) (abstract).
Sethu et al., Anal. Chem., 76(21):6247-6253 (2004) (abstract).
Sethu et al., Anal. Chem., 78(15):5453-5461 (2006) (abstract).
Vandelinder et al., Anal. Chem., 78(11):3765-3771 (2006) (abstract).
Vandelinder et al., Anal. Chem., 79(5):2023-2030 (2007) (abstract).
Vindelov et al., "A detergent-trypsin method for the preparation of nuclei for flow cytometric DNA analysis," Cytomertry 3 (5): 323 (1983).
Watson, "Isolation and use of mammalian cell nuclei," Life Science Quarterly (Jul. 2000).
Tai et al., "Automatic microfluidic platform for cell separation and nucleus collection," Biomed Microdevices, Kluwer Academic Publishers, BO, vol. 9, No. 4, May 17, 2007, pp. 533-543.
Chien-Hsuan Tai et al., "Automatic microfluidic platform for cell separation and nucleus collection," Biomedical Microdevices, Kluwer Academic Publishers, BO, vol. 9, No. 4, pp. 533-543, ISSN 1572-8781, May 17, 2007.

* cited by examiner

METHODS AND SYSTEMS FOR DNA ISOLATION ON A MICROFLUIDIC DEVICE

CROSS-REFERENCE TO RELATED APPLICATION

This application is a divisional of and claims priority to U.S. patent application Ser. No. 12/505,195, filed on Jul. 17, 2009, which is incorporated herein by reference in its entirety. This application is related to U.S. patent application Ser. No. 12/505,202, filed on Jul. 17, 2009, entitled "METHODS AND SYSTEMS FOR MICROFLUIDIC DNA SAMPLE PREPARATION," naming Weidong Cao, Hiroshi Inoue and Kevin Louder as inventors, which is incorporated herein by this reference in its entirety.

BACKGROUND

1. Field of the Invention

The present invention relates to methods and systems for the isolation of DNA on a microfluidic device and the subsequent analysis of the DNA on the microfluidic device. More specifically, embodiments of the present invention relate to methods and systems for the isolation of DNA from patient samples on a microfluidic device and use of the DNA for performing amplification reactions, such as PCR, and detection, such as thermal melt analysis, on the microfluidic device.

2. Description of Related Art

The detection of nucleic acids is central to medicine, forensic science, industrial processing, crop and animal breeding, and many other fields. The ability to detect disease conditions (e.g., cancer), infectious organisms (e.g., HIV), genetic lineage, genetic markers, and the like, is ubiquitous technology for disease diagnosis and prognosis, marker assisted selection, correct identification of crime scene features, the ability to propagate industrial organisms and many other techniques. Determination of the integrity of a nucleic acid of interest can be relevant to the pathology of an infection or cancer. One of the most powerful and basic technologies to detect small quantities of nucleic acids is to replicate some or all of a nucleic acid sequence many times, and then analyze the amplification products. PCR is perhaps the most well-known of a number of different amplification techniques.

The basic steps of nucleic acid, such as DNA, isolation are disruption of the cellular structure to create a lysate, separation of the soluble nucleic acid from cell debris and other insoluble material, and purification of the DNA of interest from soluble proteins and other nucleic acids. Historically, organic extraction (e.g., phenol:chloroform) followed by ethanol precipitation was performed to isolate DNA. Disruption of most cells is performed by chaotropic salts, detergents or alkaline denaturation, and the resulting lysate is cleared by centrifugation, filtration or magnetic clearing. The DNA can then be purified from the soluble portion of the lysate. When silica matrices are used, the DNA is eluted in an aqueous buffer such as Tris-EDTA (TE) or nuclease-free water.

DNA isolation systems for genomic, plasmid and PCR product purification are historically based on purification by silica. Regardless of the method used to create a cleared lysate, the DNA of interest can be isolated by virtue of its ability to bind silica in the presence of high concentrations of chaotropic salts (Chen and Thomas, *Anal Biochem* 101:339-341, 1980; Marko et al., *Anal Biochem* 121:382-387, 1982; Boom et al., *J Clin Microbiol* 28:495-503, 1990). These salts are then removed with an alcohol-based wash and the DNA eluted in a low ionic strength solution, such as TE buffer or water. The binding of DNA to silica may be driven by dehydration and hydrogen bond formation, which competes against weak electrostatic repulsion (Melzak et al., *J Colloid and Interface Science* 181:635-644, 1996). Hence, a high concentration of salt will help drive DNA adsorption onto silica, and a low concentration will release the DNA.

Recently, new methods for DNA purification have been developed which take advantage of the negatively charged backbone of DNA to a positively charged solid substrate (under specific pH conditions), and eluting the DNA using a change in solvent pH (ChargeSwitch® technology, Invitrogen, Corp., Carlsbad, Calif.; see, for example, U.S. Pat. No. 6,914,137 and International Published Application No. 2006/004611). Whatman has an alternate technology (FTA® paper) that utilizes a cellulose based solid substrate impregnated with a lysis material that lyses cells, inactivates proteins, but captures DNA in the cellulose fibers, where it is retained for use in downstream applications (see, for example, U.S. Pat. No. 6,322,983).

The use of nuclear extracts was reported in 1983 (Dignani et al., *Nucl Acids Res* 11:1475-1489, 1983). There are several commercial kits that allow for the selective lysis of a cellular membrane while allowing for the purification of cellular organelles, including nuclei. Sigma and Pierce are two providers of commercial kits. These kits utilize centrifugation for the collection of nuclei. There are two patents that describe purifying nuclei from cells. U.S. Pat. No. 5,447,864 describes using a DNA mesh to capture intact cell nuclei on a membrane to capture nuclei for various applications. A membrane is extended across the forward end of a pipette tip device and the DNA from lysed nuclei is used to capture the remaining intact nuclei. U.S. Pat. No. 6,992,181 B2 describes the use of a CD device for the purification of DNA or cell nuclei. This method requires moving parts and centrifugal force to isolate DNA and or cell nuclei, using a barrier in the channel to impede flow of DNA and nuclei. Both patents describe the capture of nuclei and/or DNA and subsequent steps of washing are also required for their systems.

Various papers have described the capture of nuclei or white blood cells for downstream use in PCR reactions. If only the white blood cells are isolated, the primary inhibitor of PCR reactions, haemoglobin, is removed, yielding higher efficiencies in PCR, (Cheng et al., *Nucl Acids Res* 24:380-385, 1996). Another approach (Service, *Science* 282:399-401, 1998) involves mixing blood with a salt solution that lyses the cells. The lysate is then introduced into a chamber containing a glass wall on which DNA binds by charge interaction, while the rest of the sample is ejected. DNA must then be washed and is eluted to another chamber. Another paper describes a microfluidic platform for cell separation and nucleus collection that uses dielectrophoresis (DEP) forces to separate cells in a continuous flow system. After a specific cell was captured a lysis buffer was added and the nucleus of the cell can then be collected to study nuclear proteins. The ability to perform PCR on a single captured nucleus was demonstrated by Li et al. (*Eukaryotic Cell* 2:1091-1098, 2003). A nucleus extracted by a micropipette was added directly to a PCR reaction for the detection of a specific gene sequence. This paper demonstrates that nuclei added directly to a PCR reaction can be used to deliver DNA template, and assays for specific gene targets can be conducted using nuclei isolated from cells.

The most significant problems with the current technologies are that they require specific buffers for DNA binding and washing, most of which are not compatible with down stream applications such as PCR, and they have a wide range of efficiencies in the overall quantity of DNA that is purified.

This can be a significant problem when samples are to be used in microfluidics. The multiple reagents that are typically required for DNA purification would demand that moving parts, such as valves, be constructed into a microfluidic device for the introduction of multiple reagents in a solid phase extraction. In a microfluidic system, solid phase extraction or the use of multiple reagents is complicated and can lead to system failures. Commercial assays that are sold by Sigma and Pierce for cellular organelle purification do not use a filtration process for nuclei capture. Instead, they use centrifugal force to collect the nuclei.

In addition, microfluidic devices have been designed to do cell sorting of whole blood and separating white blood cells from red blood cells and plasma. However, such devices do not maximize the removal of proteins, lipids, and other cellular components that may inhibit PCR in a microfluidic system.

Although the various methods exist to capture nuclei for use in down stream application or to separate specific cells from a sample population, none of these methods describes a device that is capable of extracting cell nuclei and performing PCR assays on the nuclei using the same device. Thus, there is a need to develop improved systems and methods for DNA purification through nuclei isolation and integrated PCR detection of genetic sequences in microfluidic devices.

SUMMARY OF THE INVENTION

The present invention relates to methods and systems for the isolation of DNA on a microfluidic device and the subsequent analysis of the DNA on the microfluidic device. More specifically, embodiments of the present invention relate to methods and systems for the isolation of DNA from patient samples on a microfluidic device and the use of the DNA for performing amplification reactions, such as PCR, and detection, such as thermal melt analysis, on the microfluidic device.

In one aspect, the present invention provides a method of isolating DNA from cells in a sample. According to this aspect, the method comprises: (a) selectively lysing the cellular membranes of the cells in the sample without lysing the nuclear membranes of the cells to produce intact nuclei from the cells; (b) separating the intact nuclei from the sample by a nuclei size exclusion barrier in a nuclei separation region of a microfluidic device; (c) resuspending the separated nuclei in an elution buffer in the nuclei separation region of the microfluidic device; (d) delivering the resuspended nuclei to a nuclei lysis region of a microfluidic device and (e) lysing the resuspended nuclei to release the DNA in the nuclei lysis region of the microfluidic device.

In some embodiments, the sample is a patient sample which can be, for example, a blood sample, a urine sample, a saliva sample, a sputum sample, a cerebrospinal fluid sample, a body fluid sample or a tissue sample. In other embodiments, the patient sample contains white blood cells. In additional embodiments, the patient sample is a blood sample that is first enriched for white blood cells prior to the selective lysis of the cellular membrane. In some embodiments, the enrichment of white blood cells is performed by filtration. In additional embodiments, the enrichment of white blood cells is performed using antibodies. In some embodiments, the antibodies are coupled to a solid phase, such as beads, magnetic beads, particles, polymeric beads, chromatographic resin, filter paper, a membrane or a hydrogel.

In some embodiments, the selective lysis is performed by contacting the patient sample, such as whole blood or a sample after white blood cell enrichment, with a nuclei isolation buffer that selectively permeabilizes cellular membranes while leaving the nuclei of the cells intact. In other embodiments, the selective lysis is performed using a hypotonic lysis buffer that contains a weak detergent. In further embodiments, the patient sample and the hypotonic lysis buffer are mixed in a 1:1 ratio. In additional embodiments, the selective lysis of the cellular membranes totally lyses red blood cells. In some embodiments, the patient sample and the nuclei isolation buffer are mixed off the microfluidic device and then added to the nuclei separation region of the microfluidic device. In other embodiments, the patient sample and the nuclei isolation buffer are mixed in a cell lysis region of a microfluidic device.

In some embodiments, the nuclei separation region in the microfluidic device has a nuclei size exclusion barrier for separating the nuclei from the rest of the patient sample, including the cell debris. In other embodiments, the nuclei size exclusion barrier is a system of pillars prefabricated into the nuclei separation region to retard the nuclei on one side of the nuclei separation region. In other embodiments, the nuclei size exclusion barrier is a filter system constructed to retard the nuclei on one side of the nuclei separation region. In additional embodiments, the nuclei size exclusion barrier comprises holes along the bottom of the nuclei separation region designed to retard the nuclei on one side of the nuclei separation region. In some embodiments, flow through the nuclei size exclusion barrier is driven by a pressure differential.

In some embodiments, the elution buffer is a buffer in which the nuclei are compatible. In other embodiments, the elution buffer is an amplification reaction buffer that may contain the non-assay specific amplification reagents. In additional embodiments, the amplification reaction buffer is a PCR buffer that may contain the non-assay specific PCR reagents. In further embodiments, the elution buffer contains a dye that binds to DNA. In additional embodiments, the dye is useful for quantifying the amount of DNA in the channel. In some embodiments, the intact nuclei are resuspended in the elution buffer by flow of the elution buffer through the nuclei separation region and across the nuclei size exclusion barrier, which flow is driven by a pressure differential. In other embodiments, the resuspended nuclei are driven to a nuclei lysis region of a microfluidic device. In additional embodiments, the nuclei are lysed by heat in the nuclei lysis region to release the DNA from the nuclei. In some embodiments, the nuclei are subjected to heat in a nuclei lysis region prior to an amplification reaction. In other embodiments, the nuclei are subjected to heat during the amplification reaction and the nuclei lysis region is the initial region of microfluidic device in which the amplification reaction is conducted.

In another aspect, the present invention provides a method of determining presence or absence of a nucleic acid in a patient sample. According to this aspect, the method comprises: (a) selectively lysing the cellular membranes of cells in the patient sample without lysing the nuclear membranes of the cells to produce intact nuclei from the cells; (b) separating the intact nuclei from the patient sample by a nuclei size exclusion barrier in a nuclei separation region of a microfluidic device; (c) resuspending the separated nuclei in an elution buffer in the nuclei separation region of the microfluidic device; (d) delivering the resuspended nuclei to a nuclei lysis region of a microfluidic device; (e) lysing the separated nuclei to release the nucleic acid in the microfluidic device; (f) amplifying the nucleic acid in the microfluidic device; and (g) determining the presence or absence of an amplified product, wherein the presence of the amplified product indicates the presence of the nucleic acid in the patient sample.

In some embodiments, the patient sample is as described above. In other embodiments, the patient sample is first enriched for white blood cells prior to the selective lysis of the cellular membrane as described above. In other embodiments, the selective lysis is performed as described above. In additional embodiments, the nuclei separation region of the microfluidic device has a nuclei size exclusion barrier for separating the nuclei from the rest of the patient sample as described above. In further embodiments, the elution buffer is a buffer as described above. In other embodiments the nuclei are lysed by heat to release the nucleic acid from the nuclei as described above.

In some embodiments, the resuspended nuclei or the isolated nucleic acid from a nuclei lysis region of the microfluidic device is introduced into a single reaction channel in a microfluidic device for amplification and analysis. In other embodiments, the resuspended nuclei or the isolated nucleic acid from a nuclei lysis region of the microfluidic device is introduced into two or more reaction channels in a microfluidic device for amplification and analysis. In further embodiments, the resuspended nuclei or the isolated nucleic acid is introduced into the reaction channels by application of a pressure differential. In some embodiments, amplification reaction buffer that may contain the non-assay specific amplification reagents is added to the resuspended nuclei or the isolated nucleic acid that are in a non-amplification elution buffer prior to introduction into the reaction channels. In additional embodiments, the quantity of resuspended nuclei or the isolated DNA is determined prior to introduction into the reaction channels. In further embodiments, assay specific reagents are added to the resuspended nuclei or the isolated nucleic acid. In some embodiments, the assay specific reagents are added prior to introduction of the resuspended nuclei or isolated nucleic acid into the reaction channels. In other embodiments, the assay specific reagents are added after introduction of the resuspended nuclei or the isolated nucleic acid into the reaction channels. In additional embodiments, the amplification reaction is a polymerase chain reaction. In further embodiments, the presence or absence of amplified product is detected. In some embodiments, the detection of amplified product is performed by thermal melt analysis. In other embodiments, the detection of amplified product is performed by using a label that changes intensity upon the presence of amplified product.

In some embodiments, steps (b)-(g) and optionally step (a) are performed in one microfluidic device. In other embodiments steps (b) and (c) and optionally step (a) are performed in one microfluidic device and steps (e)-(g) are performed in a second microfluidic device. In further embodiments, steps (b)-(e) and optionally step (a) are performed in one microfluidic device and steps (f) and (g) are performed in a second microfluidic device.

In an additional aspect, the present invention provides a microfluidic system for isolating DNA from cells in a patient sample. According to this aspect, the microfluidic system comprises a cell lysis region in which the cellular membranes of the cells in the patient sample are selectively lysed without lysing the nuclear membranes of the cells to produce intact nuclei from the cells. The microfluidic system also comprises a nuclei separation region in a microfluidic device which blocks intact nucleic while passing the rest of the patient sample driven by a pressure differential to carry away components of the patient sample smaller than the intact nuclei and the intact nuclei resuspended in an elution buffer being driven by a pressure differential to carry intact nuclei out of the nuclei size exclusion region. The microfluidic system further comprises a nuclei lysis region in which the nuclear membranes of the intact nuclei are lysed to release the DNA.

In some embodiments, the nuclei separation region includes a nuclei size exclusion barrier as described above. In other embodiments, the cell lysis region is off the microfluidic device. In additional embodiments, the cell lysis region is in a channel in the microfluidic device. In further embodiments, the nuclei lysis region comprises a source of heat sufficient to lysis the nuclear membranes of the intact nuclei and release the DNA.

In some embodiments, the microfluidic system further comprises a control system which controls the flow of the patient sample through the nuclei separation region and controls the flow of the elution buffer through the nuclei separation region. In other embodiments, the control system controls the flow of the patient sample and elution buffer by vacuum pressure. In further embodiments, the control system causes the patient sample to flow in a first direction and causes the elution buffer to flow in a second direction. In some embodiments, the first direction is substantially orthogonal to the second direction.

In a further aspect, the present invention provides a microfluidic system for determining presence or absence of a nucleic acid in a patient sample. According to this aspect, the microfluidic system comprises a cell lysis region, a nuclei separation region and a nuclei lysis region as described above. The microfluidic system also comprises an amplification reaction region in which the nucleic acid is amplified. The microfluidic system further comprises a detection region for determining the presence or absence of an amplified product. The microfluidic system may further comprise a control system as described above.

In some embodiments, the nuclei separation region includes a nuclei size exclusion barrier as described above. In other embodiments, the cell lysis region is off the microfluidic device. In additional embodiments, the cell lysis region is in a channel in a microfluidic device. In further embodiments, the nuclei lysis region comprises a source of heat sufficient to lysis the nuclear membranes of the intact nuclei and release the nucleic acid. In other embodiments, the source of heat is in the amplification reaction region. In some embodiments, the amplification reaction region is a PCR region. In other embodiments, the detection region is a thermal melt analysis region. In additional embodiments, the microfluidic system further comprises a nucleic acid quantification region before the amplification reaction region for quantifying the nucleic acid in the channel prior to the amplification reaction region. In some embodiments, the amplification reaction region and the detection region comprises multiple channels. In other embodiments, each channel in the amplification reaction region and the detection region receives nucleic acid from a single channel containing the nuclei size exclusion region and the nuclei lysis region. In further embodiments, two or more channels in the amplification reaction region and the detection region receive nucleic acid from a single channel containing the nuclei size exclusion region and the nuclei lysis region.

In some embodiments, optionally the cell lysis region and all of the remaining regions are in a single microfluidic device. In other embodiments, the nuclei separation region and the nuclei lysis region and optionally the cell lysis region are in one microfluidic device and the amplification reaction region and the detection region are in a second microfluidic device. In further embodiments, the nuclei separation region and optionally the cell lysis region are in one microfluidic device and the cell lysis region, amplification reaction region and detection region are in a second microfluidic device.

The above and other embodiments of the present invention are described below with reference to the accompanying drawings.

BRIEF DESCRIPTION OF THE DRAWINGS

The accompanying drawings, which are incorporated herein and form part of the specification, illustrate various embodiments of the present invention. In the drawings, like reference numbers indicate identical or functionally similar elements.

DETAILED DESCRIPTION OF PREFERRED EMBODIMENTS

Figure 1:
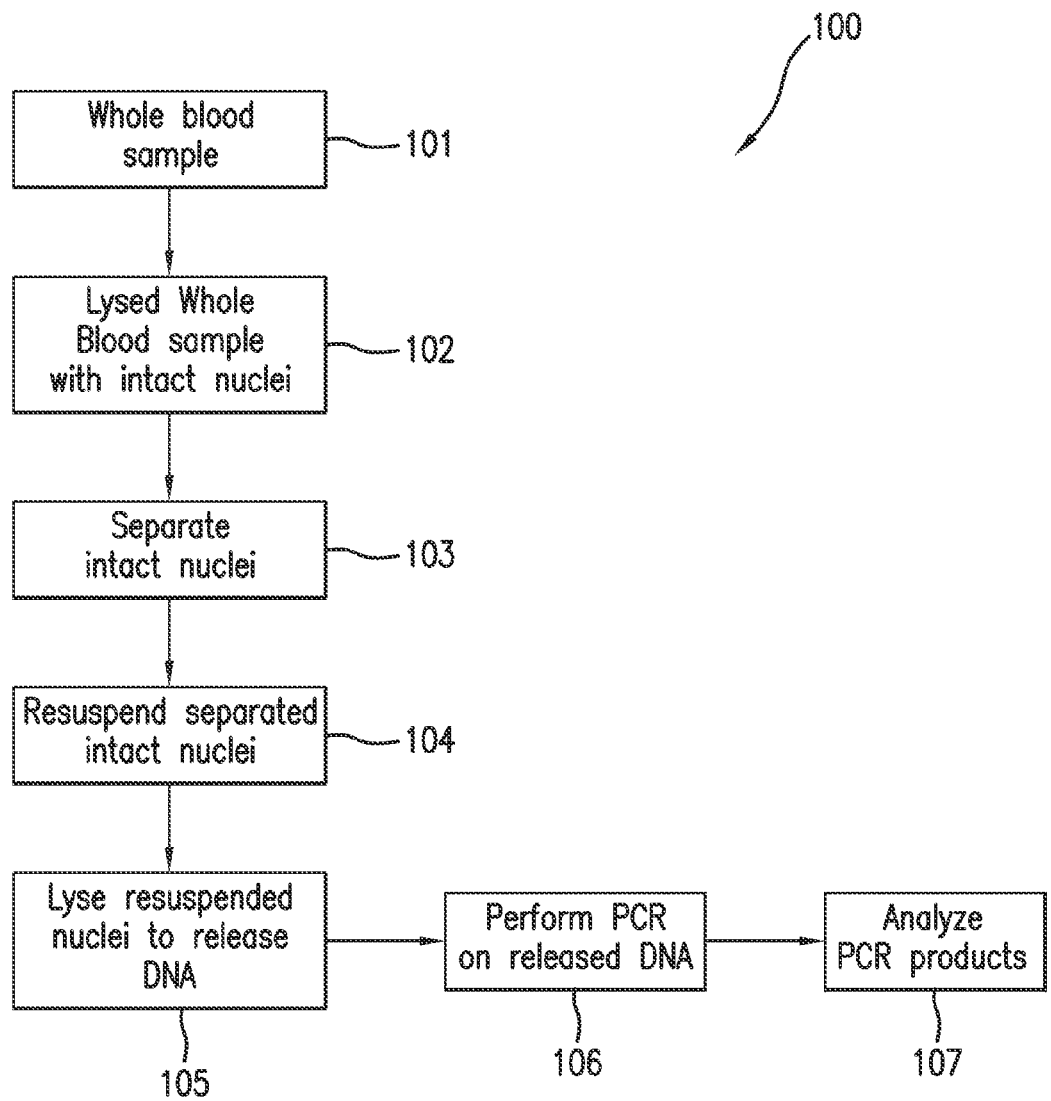
FIG. 1 illustrates a flow chart of a process for sample preparation on a microfluidic device in accordance with embodiments of the present invention.

The present invention has several embodiments and relies on patents, patent applications and other references for details known to those of the art. Therefore, when a patent, patent application, or other reference is cited or repeated herein, it should be understood that it is incorporated by reference in its entirety for all purposes as well as for the proposition that is recited.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, N.Y., Gait, *Oligonucleotide Synthesis: A Practical Approach*, 1984, IRL Press, London, Nelson and Cox (2000), Lehninger, *Principles of Biochemistry* 3rd Ed., W. H. Freeman Pub., New York, N.Y. and Berg et al. (2002) *Biochemistry*, 5th Ed., W. H. Freeman Pub., New York, N.Y., all of which are herein incorporated in their entirety by reference for all purposes.

The present invention provides methods and systems for the isolation of DNA from patient samples on a microfluidic device and the subsequent analysis of the DNA on a microfluidic device. More specifically, the present invention provides methods and systems for the isolation of DNA from patient samples on a microfluidic device and the use of the DNA for performing amplification reactions, such as PCR, and detection, such as thermal melt analysis, on a microfluidic device.

Thus, in a first aspect, the present invention provides a method of isolating DNA from cells in a patient sample comprising: (a) selectively lysing the cellular membranes of the cells in the patient sample without lysing the nuclear membranes of the cells to produce intact nuclei from the cells; (b) separating the intact nuclei from the patient sample by a nuclei size exclusion barrier in a nuclei separation region of a microfluidic device; (c) resuspending the separated nuclei in an elution buffer in the nuclei separation region of the microfluidic device; (d) delivering the resuspended nuclei to a nuclei lysis region of a microfluidic device; and (e) lysing the resuspended nuclei to release the DNA in the nuclei lysis region of the microfluidic device.

The selective lysis involves lysing the cellular membranes of the cells without lysing the nuclear membranes of the cells in the patient sample to produce intact nuclei from the cells. The patient sample may be a blood sample, a urine sample, a saliva sample, a sputum sample, a cerebrospinal fluid sample, a body fluid sample or a tissue sample. In some embodiments, the patient sample contains white blood cells. In a preferred embodiment, the patient sample is a blood sample. Since red blood cells only have a cellular membrane and do not include a nucleus, the selective lysis totally lyses the red blood cells in a patient blood sample. In some embodiments, the patient sample is first enriched for white blood cells prior to the selective lysis of the cellular membranes. Techniques for the enrichment of white blood cells are known to the skilled artisan. In some embodiments, the enrichment of white blood cells is performed by filtration. In additional embodiments, the enrichment of white blood cells is performed using antibodies. In some embodiments, the antibodies art coupled to a solid phase, such as beads, magnetic beads, particles, polymeric beads, chromatographic resin, filter paper, a membrane or a hydrogel. See, for example, U.S. Pat. Nos. 4,752,564, 5,118,428, 5,482,829 and 5,736,033, PCT International Publication No. WO 88/05331, Boyum (*Nature* 204:793-794, 1964) and VanDelinder and Groisman (*Anal Chem* 79:2023-2030, 2007). Products that are commercially available for the enrichment of white blood cells include, but are not limited to, Ficoll-Paque™ PLUS (GE Healthcare, Piscataway, N.J.), White Blood Cell Isolation (Leukasorb) Medium (Pall Corporation, East Hills, N.Y.) and Accuspin™ System (Sigma Aldrich, St. Louis, Mo.).

The selective lysis is performed by contacting the patient sample with a buffer (referred to herein as a selective lysis buffer, a lysis buffer or a nuclei isolation buffer) that selectively permeabilizes cellular membranes while leaving the nuclei of the cells intact. Nuclei isolation buffers that have these characteristics are well known to the skilled artisan. Products that include nuclei isolation buffers for selectively lysing cellular membranes are commercially available. Suitable commercial products that include such buffers, include, but are not limited to, Nuclei EZ Prep Nuclei Isolation Kit (NUC-101) (Sigma, St. Louis, Mo., USA), Nuclear/Cytosol Fractionation Kit (K266-100) (BioVision Research Products, Mountain View, Calif., USA), NE-PER Nuclear and Cytoplasmic Extraction Reagents (Pierce, Rockville, Ill., USA), Nuclear Extraction Kit (Imgenex, Corp., San Diego, Calif., USA), Nuclear Extract Kit (Active Motif, Carlsbad, Calif., USA), and Qproteome Nuclear Protein Kit (Qiagen, Valencia, Calif., USA). See also, U.S. Pat. Nos. 5,447,864, 6,852, 851 and 7,262,283. It is known that the type of nuclei in question may determine which nuclei isolation buffer will be required. See, U.S. Pat. No. 5,447,864 for a discussion of factors that can be optimized for preparing a suitable selective lysis buffer for different cell types.

In one embodiment, the selective lysis buffer is a hypotonic buffer. For example, commercial hypotonic lysis buffer can be purchased from Sigma Aldrich, Nuclei EZ lysis buffer (N 3408). A kit is also available from Sigma Aldrich, Nuclei EZ Prep Nuclei Isolation Kit (Nuc-101). A common recipe for a 10× hypotonic solution is, 100 mM HEPES, pH 7.9, with 15 mM $MgCl_2$ and 100 mM KCl. In another embodiment, the buffer is a hypotonic buffer that comprises a detergent. Suitable detergents include, but are not limited to ionic detergents, such as lithium lauryl sulfate, sodium deoxycholate, and Chaps, or non-ionic detergents, such as Triton X-100, Tween 20, Np-40, and IGEPAL CA-630. In another embodiment, the buffer is an isotonic buffer. For example, Sigma Aldrich offers a kit, CelLytic Nuclear Extraction kit, which contains an isotonic lysis buffer. A common recipie for a 5× isotonic lysis buffer is, 50 mM Tris HCl, pH 7.5, with 10 mM $MgCl_2$, 15 mM $CaCl_2$, and 1.5M Sucrose. In an additional embodiment, the buffer is an isotonic buffer that comprises a detergent which may be an ionic detergent or a non-ionic detergent.

The patient sample and lysis buffer are contacted for a period of time sufficient to effect the selective lysis. A suitable period of time may range from 1-10 minutes, preferably 2-8 minutes, more preferably 3-5 minutes. If the patient sample is a blood sample, the period of time is sufficient to totally lyse the red blood cells. In some embodiments, the patient sample and lysis buffer may be mixed in accordance with the manufacturers' recommendations. In some embodiments, the patient sample and lysis buffer are mixed in a 1:1 ratio. In other embodiments, the patient sample and lysis buffer are contacted at room temperature. In some embodiments, the patient sample and lysis buffer are contacted, such as by mixing, off a microfluidic device. This contacting could occur in vial, tube, microtiter plate, and the like.

In some embodiments, the patient sample and lysis buffer are contacted in a microfluidic device. In one embodiment, the patient sample and lysis buffer are added to a cell lysis region of the microfluidic device. This cell lysis region may be a chamber or a channel. In another embodiment, the patient sample can be added to one port of a microfluidic device and the lysis buffer added to a second port. The patient sample and lysis buffer are then flowed together in a cell lysis region of the microfluidic device. The flow of the patient sample, lysis buffer and the contacted mixture can be driven by a pressure differential. Examples of techniques for contacting the patient sample and lysis buffer in a microfluidic device are disclosed in U.S. application Ser. No. 12/505,202, filed on Jul. 17, 2009, entitled "METHODS AND SYSTEMS FOR MICROFLUIDIC DNA SAMPLE PREPARATION," naming Weidong Cao, Hiroshi Inoue and Kevin Louder as inventors, incorporated herein by reference.

In those embodiments in which the patient sample and lysis buffer are contacted off a microfluidic device, the selectively lysed sample is added to a nuclei separation region of a microfluidic device. In those embodiments in which the patient sample and the lysis buffer are contacted in a microfluidic device, the selectively lysed sample is driven to a nuclei separation region of the microfluidic device. The nuclei separation region may be a chamber or a channel in a microfluidic device. The nuclei separation region includes a nuclei size exclusion barrier that is capable of separating the intact nuclei from the remainder of the rest of the patient sample, including cell debris. In some embodiments, the nuclei size exclusion barrier is a system of pillars prefabricated into the nuclei separation region to retard the nuclei on one side of the nuclei separation region. In other embodiments, the nuclei size exclusion barrier is a filter system constructed to retard the nuclei on one side of the nuclei separation region. In additional embodiments, the nuclei size exclusion barrier comprises holes along the bottom of the nuclei separation region designed to retard the nuclei on one side of the nuclei separation region. In some embodiments, flow through the nuclei size exclusion barrier is driven by a pressure differential.

In some embodiments, the nuclei exclusion barrier has an exclusion size in the range of 2.7 µm to 5.0 µm. In other embodiments, the nuclei exclusion barrier has an exclusion size in the range of 2.7 µm to 4 µm. In additional embodiments, the nuclei exclusion barrier has an exclusion size in the range of 2.7 µm to 3 µm. In further embodiments, the nuclei exclusion barrier has an exclusion size of 2.7 µm.

After the intact nuclei have been separated from the rest of the patient sample including the cell debris, the intact nuclei are resuspended in an elution buffer. The elution buffer is one in which the nuclei are compatible and one that is compatible with any downstream processing of the DNA that is to be isolated from the nuclei. If the DNA is to be subjected to an amplification reaction, the elution buffer may be an amplification reaction buffer. In some embodiments, the amplification reaction buffer may contain the non-assay specific amplification reagents. If the amplification reaction is a polymerase chain reaction, the buffer may be a PCR buffer that may contain the non-specific PCR reagents. In some embodiments, the elution buffer also contains a dye that binds to DNA. The DNA dye may be one that binds to free DNA or it may be one that binds to chromosomal DNA, that is, the dye is able to cross the nuclear membrane and bind to the DNA in the intact nuclei. DNA dyes are well known to the skilled artisan. Examples of DNA dye include, but are not limited to, 4',6-diamidino-2-phenylindole (DAPI), SYBR® Green, SYBR® GreenER™ and PicoGreen (Invitrogen Corp., Carlsbad, Calif.) and LC Green (Idaho Technology, Salt Lake City, Utah). In some embodiments, the DNA dye is useful for quantifying the amount of DNA that has been isolated or that is to be used for downstream processing.

In some embodiments, the intact nuclei are resuspended in the elution buffer by flow of the elution buffer through the nuclei separation region and across the nuclei size exclusion barrier, which flow is driven by a pressure differential. Once the intact nuclei have been resuspended in the elution buffer, the resuspended nuclei are driven to a nuclei lysis region of a microfluidic device. In one embodiment, the nuclei are lysed by heat in the nuclei lysis region to release the DNA from the nuclei. In some embodiments, the nuclei are subjected to heat in a nuclei lysis region prior to an amplification reaction. In other embodiments, the nuclei are subjected to heat during the amplification reaction, and the nuclei lysis region is in the initial portion of a microfluidic device in which the amplification reaction is conducted. In some embodiments, the nuclei lysis region is in the same microfluidic device as the nuclei separation region. In other embodiments, the nuclei lysis region is in a different microfluidic chip than the nuclei separation region.

In a second aspect, the present invention provides a method of determining the presence or absence of a nucleic acid in a patient sample comprising: (a) selectively lysing the cellular membranes of the cells in the patient sample without lysing the nuclear membranes of the cells to produce intact nuclei from the cells; (b) separating the intact nuclei from the patient sample by a nuclei size exclusion barrier in a nuclei separation region of a microfluidic device; (c) resuspending the separated nuclei in an elution buffer in the nuclei separation region of the microfluidic device; (d) delivering the resuspended nuclei to a nuclei lysis region of a microfluidic device; (e) lysing the resuspended nuclei to release the nucleic acid in the nuclei lysis region of the microfluidic device; (f) amplifying the nucleic acid in a microfluidic device; and (g) determining the presence or absence of an amplified product.

In some embodiments, the patient sample is as described above. In other embodiments, the patient sample is first enriched for white blood cells prior to the selective lysis of the cellular membrane as described above. In some embodiments, the selective lysis is performed as described above. In additional embodiments, the nuclei separation region of the microfluidic device has a nuclei size exclusion barrier for separating the nuclei from the rest of the patient sample as described above. In further embodiments, the elution buffer is a buffer as described above. In other embodiments the nuclei are lysed by heat to release the nucleic acid from the nuclei as described above.

After lysing the nuclei to release the nucleic acid, the nucleic acid is then subjected to an amplification reaction. As described above, this lysis may be performed in the initial phase of the amplification reaction. In some embodiments, the amplification reaction is a polymerase chain reaction. In other embodiments, the amplification reaction is a real-time polymerase chain reaction. These polymerase chain reactions, as well as other amplification reactions, are well known to the skilled artisan.

In some embodiments, the resuspended nuclei or the isolated nucleic acid from a nuclei lysis region of the microfluidic device is introduced into a single reaction channel in a microfluidic device for amplification and analysis. In other embodiments, the resuspended nuclei or the isolated nucleic acid from a nuclei lysis region of the microfluidic device is introduced into two or more reaction channels in a microfluidic device for amplification and analysis. In further embodiments, the resuspended nuclei or isolated nucleic acid is introduced into the reaction channels by application of a pressure differential. In some embodiments, amplification reaction buffer that may contain the non-assay specific amplification reagents is added to the resuspended nuclei or the isolated nucleic acid in a non-amplification elution buffer prior to introduction into the reaction channels. In additional embodiments, the quantity of resuspended nuclei or the isolated nucleic acid, such as DNA, is determined prior to introduction into the reaction channels. In further embodiments, assay specific reagents are added to the resuspended nuclei or the isolated nucleic acid. In some embodiments, the assay specific reagents are added prior to introduction of the resuspended nuclei or the isolated nucleic acid into the reaction channels. In other embodiments, the assay specific reagents are added after introduction of the resuspended nuclei or the isolated nucleic acid into the reaction channels. In some embodiments, the pressure differential, such as a vacuum, is applied from the end of the reaction channels and pulls the elution buffer, which may be PCR reaction buffer, into the nuclei separation chamber to resuspend the nuclei. In other embodiments, the pressure differential also pulls the PCR reaction buffer, if it is not the elution buffer, and the assay specific reagents to mix with the resuspended nuclei before the reaction mixture is pulled into the reaction channels. In additional embodiments, the amplification reaction is a polymerase chain reaction.

In some embodiments, the presence or absence of amplified product is detected. In other embodiments, the detection of amplified product is performed by thermal melt analysis. In further embodiments, the detection of amplified product is performed by using a label that changes intensity upon the presence of amplified product. Methods for the detection of amplified products, including thermal melt analysis, are well known to the skilled artisan.

In some embodiments, steps (b)-(g) and optionally step (a) are performed in one microfluidic device. In other embodiments steps (b) and (c) and optionally step (a) are performed in one microfluidic device and steps (e)-(g) are performed in a second microfluidic device. In further embodiments, steps (b)-(e) and optionally step (a) are performed in one microfluidic device and steps (f) and (g) are performed in a second microfluidic device. Microfluidic methods and systems for amplification and detection of nucleic acids are known in the art. See, for example, U.S. Patent Application Publication Nos. 2005/0042639, 2008/0003588, 2008/0003593, 2008/0176230, 2009/0053726 and 2009/0111149, each incorporated herein by reference.

FIG. 1 is a flow chart illustrating a process 100 for the isolation of DNA from a patient sample (such as blood sample), amplification of the isolated DNA and analysis of amplified products in accordance with one embodiment of the present invention. In step 101, whole blood sample from a patient is obtained. In step 102, a hypotonic lysis buffer is added to the whole blood sample, for example, in a ratio of 1:1 (v:v), and incubated at room temperature for approximately three minutes to obtain a lysed whole blood sample with intact nucleic. In step 103, the intact nuclei are separated from the lysed whole blood sample. In one embodiment, a predetermined amount of the lysed blood sample with intact nuclei are delivered to a nuclei separation region of a microfluidic device and a pressure differential (such as a vacuum) is applied in a direction that will allow for the removal of all of the sample components except intact nuclei through a nuclei size exclusion barrier into a waste reservoir.

In step 104, the intact nuclei are resuspended in an elution buffer. In one embodiment, a pressure differential is applied in an alternate direction to that in step 103 to pull the elution buffer from a reservoir into the nuclei separation region to resuspend the intact nuclei. In one embodiment, the elution buffer can be a PCR reaction buffer. In step 105, the resuspended intact nuclei are delivered to a nucleic lysis region of a microfluidic device and the nuclei are lysed to release the DNA. In one embodiment, the pressure differential used in step 103 delivers the resuspended nuclei to the nuclei lysis region. In another embodiment, PCR assay specific reagents are pulled from a reagent reservoir into the resuspended nuclei/elution buffer mixture by the same pressure differential (such as a vacuum). The released DNA is then introduced into an amplification region of microfluidic device and an amplification reaction, such as a polymerase chain reaction, is performed in step 106. In step 107, the PCR products are analyzed, such as by a thermal melt analysis.

In a third aspect, the present invention provides a microfluidic system for isolating DNA from cells in a patient sample. According to this aspect, the microfluidic system comprises a cell lysis region in which the cellular membranes of the cells in the patient sample are selectively lysed without lysing the nuclear membranes of the cells to produce intact nuclei from the cells. The microfluidic system also comprises a nuclei separation region in a microfluidic device which blocks the passage of intact nucleic while passing the rest of the patient sample driven by a pressure differential to carry away components of the patient sample smaller than the intact nuclei, and wherein the intact nuclei resuspended in an elution buffer are driven by a pressure differential to carry intact nuclei out of the nuclei size exclusion region. The microfluidic system further comprises a nuclei lysis region in which the nuclear membranes of the intact nuclei are lysed to release the DNA.

Figure 2:
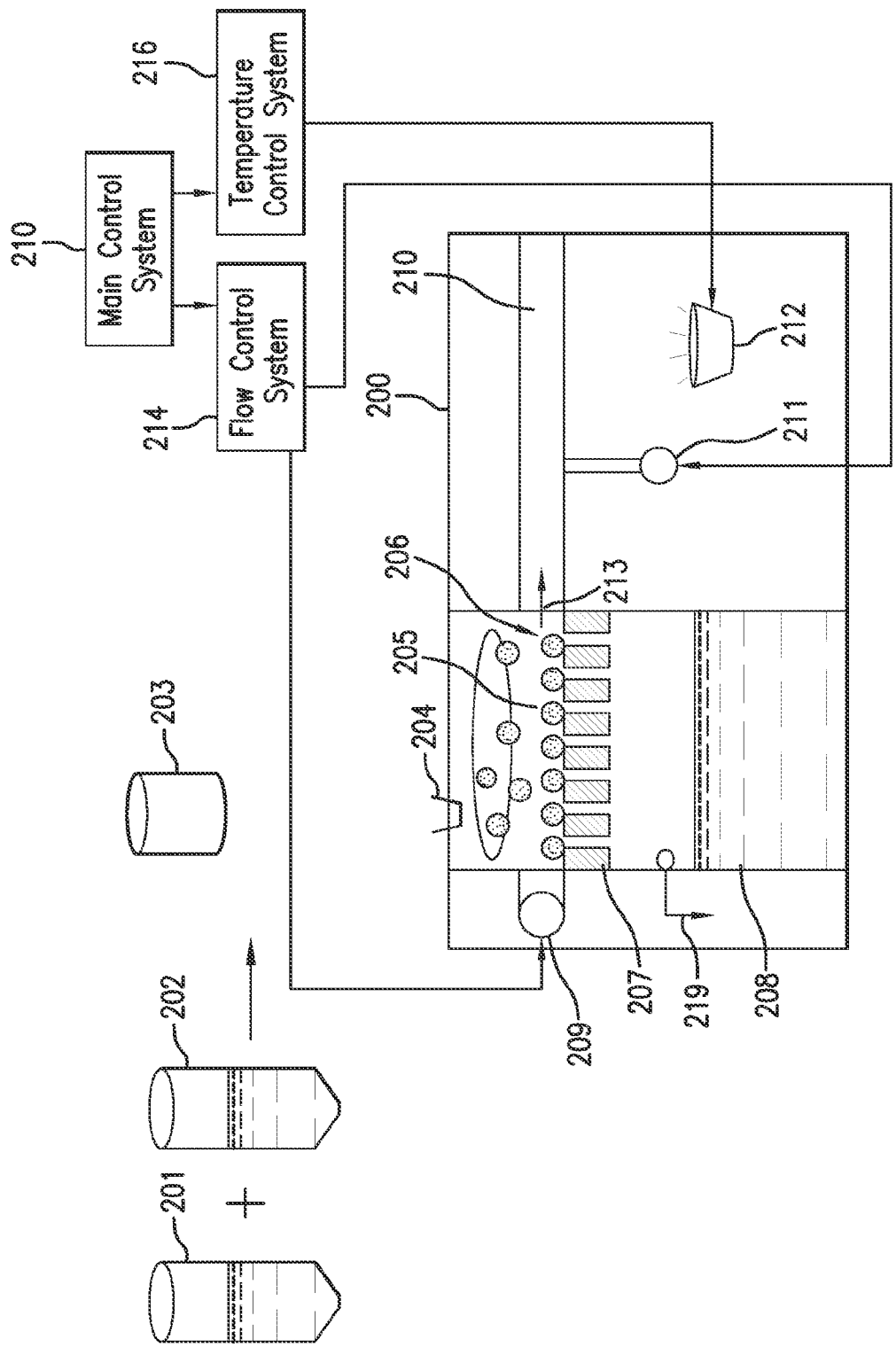
FIG. 2 illustrates a system for sample preparation on a microfluidic device in accordance with embodiments of the present invention.

An example of a suitable system for use in accordance with certain aspects of the present invention is illustrated in connection with FIG. 2. As illustrated in FIG. 2, the system includes a cell lysis region which includes a sample chamber 201, a lysis buffer chamber 202 and a cell lysis chamber 203.

As illustrated in FIG. 2, the cell lysis region may be off a microfluidic device. It is also contemplated that the cell lysis region may be on a microfluidic device. In this embodiment, the sample chamber and lysis buffer chambers are in a microfluidic device and flow into a connected channel to mix together in a cell lysis portion of the channel. Examples of cell lysis regions in a microfluidic device are disclosed in U.S. application Ser. No. 12/505,202, filed on Jul. 17, 2009, entitled "METHODS AND SYSTEMS FOR MICROFLUIDIC DNA SAMPLE PREPARATION," naming Weidong Cao, Hiroshi Inoue and Kevin Louder as inventors, incorporated herein by reference.

Returning to the system shown in FIG. 2, after lysis, the sample is delivered through port 204 to a nuclei separation region 205 of a microfluidic device 200. If the cell lysis region is in the microfluidic device, the sample is delivered to the nuclei separation region. The nuclei separation region 205 includes a nuclei size exclusion barrier 207 for separating intact nuclei 206 from the waste which passes to waste reservoir 208. The waste includes all of the components of the sample other than the intact nuclei. The nuclei size exclusion barrier is as described above. As illustrated in FIG. 2, the system also comprises an elution buffer port 209 in fluid communication with the nuclei separation region 205 for providing elution buffer to the nuclei separation region 205. Introduction of the elution buffer by, for example, a pressure differential resuspends the isolated intact nuclei and carries the resuspended nuclei out of the nuclei separation region 205 and into a nuclei lysis region 210.

As illustrated in FIG. 2, the system includes the nuclei lysis region 210 in which the nuclear membranes of the intact nuclei are lysed to release the DNA. The nuclei lysis region 210 is in fluid communication with the nuclei separation region 205. The nuclei lysis region may include a heat source, such as a lamp 212, sufficient to lyse the nuclear membranes. The system may further contain an assay specific reagent port 211 in fluid communication with the nuclei lysis region 210 for the introduction of amplification assay specific reagents into the elution buffer containing the intact nuclei or the released DNA. The assay specific reagent port 211 may be located upstream or downstream of the heat source.

The system may also include a control system which controls the flow of the patient sample through the nuclei separation region, the flow of the elution buffer through the nuclei separation region, the flow of the assay specific reagents to the nuclei lysis region and the heat supplied to the nuclei lysis region. In some embodiments, the control system comprises a main controller 210 which communicates with a flow control system 214 and a temperature control system 216. As those skilled in the art will recognize, many options exist for the main controller 210, one example being a general purpose computer and another being a special purpose computer. Other specialized control equipment in the prior art could also serve the purpose of the main controller 210.

In some embodiments, the flow control system 214 controls the flow of the patient sample through the port 204 and into the nuclei separation region 205. Flow control system 214 also controls the flow of the waste material through the nuclei size exclusion barrier 207 and into the waste reservoir 208 such as, for example, by vacuum port 219. Flow control system 214 further controls the flow of the elution buffer through the elution buffer port which resuspends the isolated intact nuclei and carries the resuspended nuclei out of the nuclei separation region 205 and into the nuclei lysis region 210. In other embodiments, flow control system controls 214 controls the flow of the assay specific reagents through port 211 and into the nuclei lysis region 210 for the introduction of amplification assay specific reagents into the elution buffer containing the intact nuclei or the released DNA.

In some embodiments, the flow control system 214 controls the flow of the patient sample and elution buffer by a pressure differential, such as by vacuum pressure. In other embodiments, the flow control system 214 causes the patient sample to flow in a first direction and causes the elution buffer to flow in a second direction. In some embodiments, the first direction is substantially orthogonal to the second direction. In other embodiments, a valve 213, shown in FIG. 2, separates the nuclei separation region 205 and the nuclei lysis region 210 which is controlled by the flow control system 214 to permit the resuspended nuclei and elution buffer to pass from the nuclei separation region to the nuclei lysis region 210.

In some embodiments, the temperature control system 216 controls the temperature of heat source 212 sufficient to lyse the nuclear membranes of the intact nuclei in the lysis region 210.

In another aspect, the present invention provides a microfluidic system for determining presence or absence of a nucleic acid in a patient sample. According to this aspect, the microfluidic system comprises a cell lysis region, a nuclei separation region and a nuclei lysis region as described above. The microfluidic system may further comprise a control system as described above. The microfluidic system also comprises an amplification reaction region in which the nucleic acid is amplified. The microfluidic system further comprises a detection region for determining the presence or absence of an amplified product.

Figure 3:
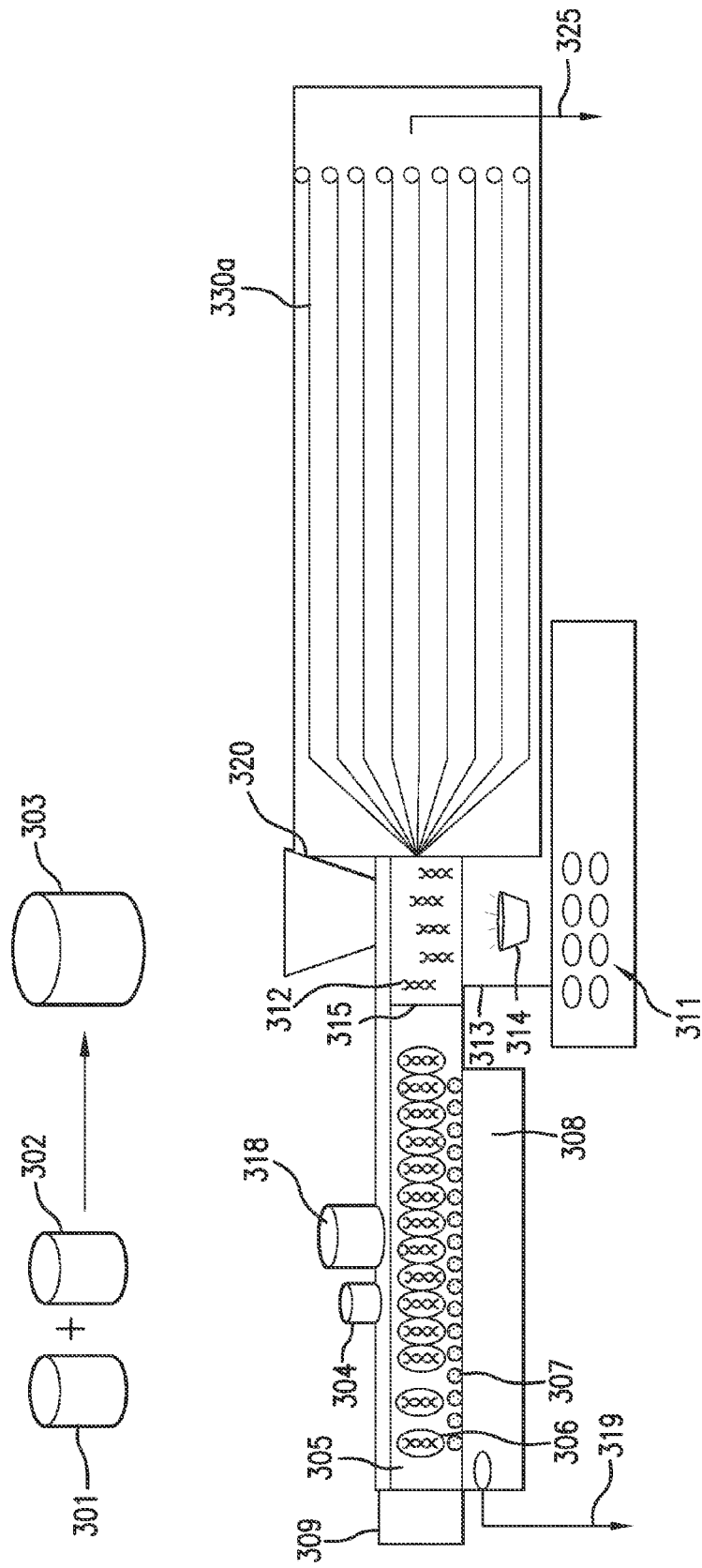
FIG. 3 illustrates a system for sample preparation on a microfluidic device in accordance with other embodiments of the present invention.

An example of a suitable system for use in accordance with certain aspects of the present invention is illustrated in connection with FIG. 3. As illustrated in FIG. 3, the system includes a cell lysis region which includes a sample chamber 301, a lysis buffer chamber 302 and a cell lysis chamber 303. As illustrated in FIG. 3, the cell lysis region may be off a microfluidic device. It is also contemplated that the cell lysis region may be included on or in a microfluidic device. In one embodiment, the sample chamber and lysis buffer chambers are in a microfluidic device and flow into a connected channel to mix together in a cell lysis portion of the channel. Examples of cell lysis regions in a microfluidic device are disclosed in U.S. application Ser. No. 12/505,202, filed on Jul. 17, 2009, entitled "METHODS AND SYSTEMS FOR MICROFLUIDIC DNA SAMPLE PREPARATION," naming Weidong Cao, Hiroshi Inoue and Kevin Louder as inventors, incorporated herein by reference.

Returning to the system shown in FIG. 3, after cell lysis, the sample is delivered through port 304 to a nuclei separation region 305 of the microfluidic device. If the cell lysis region is in the microfluidic device, the sample is delivered to the nuclei separation region 305. The nuclei separation region 305 includes a nuclei size exclusion barrier 307 for separating intact nuclei 306 containing nucleic acid from the waste which passes to waste reservoir 308. In preferred embodiments, the waste includes all of the components of the sample other than the intact nuclei. The nuclei size exclusion barrier is as described above. As illustrated in FIG. 3, the system also comprises an elution buffer port 309 in fluid communication with the nuclei separation region 305 for providing elution buffer to the nuclei separation region 305. The system may contain a second elution buffer port 318 in fluid communication with the nuclei separation region 305.

In operation, the sample is delivered through port 304 to the nuclei separation region 305 of the microfluidic device. In one embodiment, a vacuum is then applied in the Y-direction, such as, for example, from the vacuum port 319 located in the waste reservoir 308. This will pull all the sample waste into the waste reservoir while the intact nuclei are prevented from passing to the waste reservoir by the nuclei size exclusion barrier 307. A vacuum is then applied in the X-direction, such as, for example, by the vacuum port 325 located at the end of the microfluidic channels 330a. This will allow for the introduction of the elution buffer from the elution buffer port 309 into the nuclei separation region 305 to resuspend the isolated intact nuclei and to carry the resuspended nuclei out of the nuclei separation region 305, as described above in connection with FIG. 2.

In another embodiment, the nuclei separation region 305 is filled with elution buffer through either elution buffer port 309 or 318 prior to the delivery of the lysed sample to the nuclei separation region. In one embodiment, the nuclei separation region 305 is pre-filled with elution buffer by applying pressure in the X-direction to reduce the production of bubbles. The lysed sample mixture is then delivered to the nuclei separation region 305 in the Y-direction, either by pressure or vacuum, to allow the separation of the nuclei from the waste and removal of the waste from the nuclei separation region 305. In one embodiment, the elution buffer port 318 is included to ensure that no bubbles are created after delivery of the lysed sample to the nuclei separation region 305. As shown in FIG. 3, vacuum can be applied in the Y-direction using vacuum port 319. Introduction of the elution buffer by, for example, a pressure differential, from elution buffer port 309 after separation of the nuclei resuspends the isolated intact nuclei and carries the resuspended nuclei out of the nuclei separation region 305, as described above in connection with FIG. 2.

Returning to FIG. 3, the system also includes a nuclei lysis region 312 in which the nuclear membranes of the intact nuclei are lysed to release the DNA. The nuclei lysis region 312 is in fluid communication with the nuclei separation region 305 through, in one embodiment, a valve 315 which is controlled by a flow control system (not shown). The nuclei lysis region may include a heat source 314, such as a lamp, sufficient to lyse the nuclear membranes. The system may further contain an assay specific reagent port or sipper 313 in fluid communication with the nuclei lysis region 312 for the introduction of amplification assay specific reagents 311, such as, for example, assay specific primers and probes, into the elution buffer containing the intact nuclei or the released DNA. The assay specific reagent port or sipper 313 may be located upstream or downstream of the heat source 314. In one embodiment, heat from the heat source 314 degrades the nuclei which allows for DNA to be mixed with PCR buffer and assay specific reagents prior to loading into the channels 330a.

As illustrated in FIG. 3, the microfluidic system may further comprise a nucleic acid quantification system for quantifying the nucleic acid in the channel prior to the amplification reaction region. In one embodiment, a detector 320 is aligned with the nuclei lysis region 312 to count the number of nuclei that are directed to one or more channels 330a, in order to know the exact concentration of template being included in the amplification reaction. Although FIG. 3 shows the nucleic acid quantification system aligned with the nuclei lysis region 312, it is contemplated that the nucleic acid quantification system could also be upstream or downstream of the nuclei lysis region 312. In one embodiment, the nucleic acid is quantified using a dye that binds to free DNA or chromosomal DNA, that is, the dye is able to cross the nuclear membrane and bind to the DNA in the intact nuclei. If the nucleic acid is to be quantified, the dye is added to the elution buffer. DNA dyes are well known to the skilled artisan. Examples of DNA dye include, but are not limited to, 4',6-diamidino-2-phenylindole (DAPI), SYBR® Green, SYBR® GreenER™ and PicoGreen (Invitrogen Corp., Carlsbad, Calif.) and LC Green (Idaho Technology, Salt Lake City, Utah).

As illustrated in FIG. 3, the nucleic acid is delivered into multiple channels 330a for downstream processing. However, it is contemplated that the nucleic acid could be delivered into a single channel for downstream processing. Also as illustrated in FIG. 3, the nuclei lysis region is upstream of channels 330a. However, it is contemplated that the nuclei lysis region could also be located in the upstream portion of channel 330a. In accordance with this aspect of the invention, the downstream processing may include the amplification of the nucleic acid and the detection of the amplified product. The amplification of the nucleic acid occurs in channel 330a in an amplification region (not shown) of the microfluidic device. The detection of the amplified product occurs in channel 330a in a detection region (not shown) of the microfluidic device. In some embodiments, the amplification is PCR amplification and the detection is a thermal melt analysis. Microfluidic systems for amplification and detection of nucleic acids are well known in the art. See, for example, U.S. Patent Application Publication Nos. 2005/0042639, 2008/0003588, 2008/0003593, 2008/0176230, 2009/0053726 and 2009/0111149, each incorporated herein by reference.

The system may also include a control system (not shown) which controls the flow of the patient sample through the nuclei separation region, the flow of the elution buffer through the nuclei separation region, the flow of the sample into the microchannels, and the temperature of the heat source 314. In some embodiments, the control system controls the flow of the patient sample and elution buffer by vacuum pressure. In other embodiments, the control system causes the patient sample to flow in a first direction and causes the elution buffer to flow in a second direction. In some embodiments, the first direction is substantially orthogonal to the second direction. In other embodiments, the control system also controls flow of the sample through the amplification region and the detection region. A suitable control system for use with the embodiment of FIG. 3 may comprise a main controller, a flow control system and a temperature control system, substantially as described above in connection with FIG. 2.

As illustrated in FIG. 3, the microfluidic system may include a single device with a cell lysis region locate off of the device. However as described above, it is contemplated that the cell lysis region could also be in the microfluidic device, such that all of the regions of the system are on a single device. It is also contemplated that the microfluidic system in accordance with certain aspects of the invention includes two devices with the cell lysis region off or on a device. In accordance with these certain aspects, it is contemplated that the nuclei separation region, the nuclei lysis region and optionally the cell lysis region are on one device and the amplification region and the detection region are on a second device. It is also contemplated that the nuclei separation region, the nuclei lysis region, the nucleic acid quantification region and optionally the cell lysis region are on one device and the amplification region and the detection region are on a second device. It is further contemplated that the nuclei separation region and optionally the cell lysis region are on one device and the nuclei lysis region, the amplification region and the detection region are on a second device. In addition, it is contemplated that the nuclei separation region, the nucleic acid quantification region and optionally the cell lysis region are on one device and the nuclei lysis region, the amplification region and the detection region are on a second device.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Various embodiments of this invention are described herein. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

What is claimed is:

1. A method of isolating DNA from cells in a sample comprising the steps of:
    (a) selectively lysing the cellular membranes of the cells in the sample without lysing the nuclear membranes of the cells to produce intact nuclei from the cells;
    (b) separating the intact nuclei from the sample by a nuclei size exclusion barrier in a nuclei separation region of a microfluidic device by flowing the sample through the nuclei size exclusion barrier in a first direction;
    (c) flowing an elution buffer in a second direction into the nuclei separation region of the microfluidic device to resuspend the isolated nuclei; wherein the first direction is substantially orthogonal to the second direction;
    (d) delivering the resuspended isolated nuclei to a nuclei lysis region of the microfluidic device; and
    (e) lysing the resuspended isolated nuclei in the nuclei lysis region of the microfluidic device to release the isolated DNA.

2. The method of claim 1, wherein the sample comprises a patient sample comprising whole blood.

3. The method of claim 2, wherein the selective lysis of the cellular membranes totally lyses the red blood cells.

4. The method of claim 2, wherein the patient sample is first enriched for white blood cells prior to the selective lysis of the cellular membranes.

5. The method of claim 1, wherein step (a) is performed off the microfluidic device.

6. The method of claim 1, wherein step (a) is performed in the microfluidic device.

7. The method of claim 1, wherein flow through the nuclei size exclusion barrier is driven by a pressure differential.

8. The method of claim 1, wherein the elution buffer is an amplification reaction buffer.

9. The method of claim 1, wherein the nuclei are lysed by heat.

10. A method of determining the presence or absence of a nucleic acid in a patient sample comprising the steps of:
    (a) selectively lysing the cellular membranes of cells in the patient sample without lysing the nuclear membranes of the cells to produce intact nuclei from the cells;
    (b) separating the intact nuclei from the patient sample by a nuclei size exclusion barrier in a nuclei separation region of a microfluidic device by flowing the sample through the nuclei size exclusion barrier in a first direction;
    (c) flowing an elution buffer in a second direction into the nuclei separation region of the microfluidic device to resuspend the isolated nuclei; wherein the first direction is substantially orthogonal to the second direction;
    (d) delivering the resuspended nuclei to a nuclei lysis region of a microfluidic device;
    (e) lysing the resuspended nuclei in the nuclei lysis region of the microfluidic device to release the nucleic acid;
    (f) amplifying the nucleic acid in a microfluidic device; and
    (g) determining the presence or absence of an amplified product, wherein the presence of the amplified product indicates the presence of the nucleic acid in the patient sample.

11. The method of claim 10, wherein the patient sample is whole blood.

12. The method of claim 11, wherein the patient sample is first enriched for white blood cells prior to the selective lysis of the cellular membranes.

13. The method of claim 10, wherein step (a) is performed off the microfluidic device.

14. The method of claim 10, wherein step (a) is performed in the microfluidic device.

15. The method of claim 10, wherein flow through the nuclei size exclusion barrier driven by a pressure differential.

16. The method of claim 10, wherein the elution buffer is an amplification reaction buffer.

17. The method of claim 10, wherein the nuclei are lysed by heat.

18. The method of claim 14, wherein the heat is applied as part of the amplification reaction.

19. The method of claim 10, wherein steps (b) and (c) are performed in one microfluidic device and steps (f) and (g) are performed in a second microfluidic device.

20. A method of isolating DNA from cells in a sample comprising the steps of:
    (a) selectively lysing the cellular membranes of the cells in the sample without lysing the nuclear membranes of the cells to produce intact nuclei from the cells;
    (b) separating the intact nuclei from the sample by a nuclei size exclusion barrier in a nuclei separation region of a microfluidic device by flowing the sample through the nuclei size exclusion barrier towards a waste chamber, wherein the barrier separates the nuclei separation region from the waste reservoir;
    (c) resuspending the isolated nuclei in an elution buffer in the nuclei separation region of the microfluidic device;

(d) delivering the resuspended isolated nuclei to a nuclei lysis region of the microfluidic device; and
(e) lysing the resuspended isolated nuclei in the nuclei lysis region of the microfluidic device to release the isolated DNA.

* * * * *